US009664669B2

(12) United States Patent
Ozasa et al.

(10) Patent No.: US 9,664,669 B2
(45) Date of Patent: May 30, 2017

(54) URINE SPECIMEN ANALYZING METHOD, URINE ANALYZER AND NON-TRANSITORY COMPUTER-READABLE STORAGE MEDIUM

(71) Applicant: Sysmex Corporation, Kobe-shi, Hyogo (JP)

(72) Inventors: Masatsugu Ozasa, Kobe (JP); Keisuke Tsutsumida, Kobe (JP); Kenji Hanamura, Kobe (JP); Kunio Ueno, Kobe (JP)

(73) Assignee: Sysmex Corporation, Hyogo (JP)

( * ) Notice: Subject to any disclaimer, the term of this patent is extended or adjusted under 35 U.S.C. 154(b) by 0 days.

(21) Appl. No.: 14/672,745

(22) Filed: Mar. 30, 2015

(65) Prior Publication Data

US 2015/0276592 A1 Oct. 1, 2015

(30) Foreign Application Priority Data

Mar. 31, 2014 (JP) .................................. 2014-071950

(51) Int. Cl.
*G01N 21/00* (2006.01)
*G01N 33/493* (2006.01)
*G01N 15/14* (2006.01)

(52) U.S. Cl.
CPC ....... *G01N 33/493* (2013.01); *G01N 15/1429* (2013.01); *G01N 15/1459* (2013.01)

(58) Field of Classification Search
CPC ...... G01N 21/27; G01N 21/255; G01N 21/59; G01N 2201/0621; G01N 21/431; G01N 21/05; G01N 21/31; B01D 53/30
USPC .......................... 356/436, 335–343, 437, 442
See application file for complete search history.

(56) References Cited

U.S. PATENT DOCUMENTS

| 4,986,657 A | 1/1991 | Ohe | |
| 5,449,622 A * | 9/1995 | Yabe | ...................... G01N 21/27 250/461.2 |
| 5,719,666 A | 2/1998 | Fukuda et al. | |
| 9,255,938 B2 * | 2/2016 | Mizumoto | .......... G01N 35/0092 |
| 2006/0012787 A1 * | 1/2006 | Nakayama | .......... G01N 15/1459 356/336 |

(Continued)

FOREIGN PATENT DOCUMENTS

EP 0 515 099 A1 11/1992
WO WO 2012/106294 A1 8/2012

OTHER PUBLICATIONS

Godavarti, M. et al., "Automated Particle Classification Based on Digital Acquisition and Analysis of Flow Cytometric Pulse Waveforms", *Cytometry*, vol. 24, No. 4, 1996, pp. 330-339.

*Primary Examiner* — Tarifur Chowdhury
*Assistant Examiner* — Isiaka Akanbi
(74) *Attorney, Agent, or Firm* — Brinks Gilson & Lione

(57) ABSTRACT

Disclosed is a urine specimen analyzing method which improves the detection of casts in a urine specimen by flowing a measurement sample containing a urine specimen through a flow cell, irradiating light on the measurement sample flowing through the flow cell, generating a signal waveform indicating a temporal change of intensity of light given off by the measurement sample, and detecting casts distinguishably from mucus threads contained in the urine specimen, based on information related to respective slope at both end sides of the signal waveform corresponding to each formed element contained in the urine specimen.

20 Claims, 11 Drawing Sheets

(56) References Cited

U.S. PATENT DOCUMENTS

| | | | |
|---|---|---|---|
| 2009/0050821 A1* | 2/2009 | Tanaka | G01N 15/1459 250/458.1 |
| 2009/0086202 A1* | 4/2009 | Wang | G01J 3/02 356/301 |
| 2010/0070197 A1* | 3/2010 | Wang | G01J 3/02 702/22 |

\* cited by examiner

URINE SPECIMEN ANALYZING METHOD, URINE ANALYZER AND NON-TRANSITORY COMPUTER-READABLE STORAGE MEDIUM

RELATED APPLICATIONS

This application claims priority from prior Japanese Patent Application No. 2014-071950, filed on Mar. 31, 2014, entitled "URINE SPECIMEN ANALYZING METHOD AND URINE ANALYZER", the entire contents of which are incorporated herein by reference.

BACKGROUND OF THE INVENTION

1. Field of the Invention

The present invention relates to a urine analyzing method, a urine analyzer and a non-transitory computer-readable storage medium.

2. Description of the Related Art

There are conventional urine sample analyzers which detect and count formed elements contained in urine. Casts and mucus threads are among the formed elements contained in urine. It is known that counting casts and mucus threads contained in urine has clinical significance. Mucus threads are long and narrow and have a shape similar to that of casts. Therefore, mucus threads produce noise when detecting casts.

U.S. Pat. No. 5,719,666 discloses discriminating between casts and mucus threads based on the (volume)/(length) of the detected formed element.

There is demand for more accurate identification of casts and mucus threads.

SUMMARY OF THE INVENTION

The scope of the invention is defined by the appended claims, and not by any statements within this summary.

A first aspect of the present invention relates to a urine specimen analyzing method. The method comprises: flowing a measurement sample containing a urine specimen through a flow cell; irradiating light on the measurement sample flowing through the flow cell; generating a signal waveform indicating a temporal change of intensity of light given off by the measurement sample; and detecting casts distinguishably from mucus threads contained in the urine specimen, based on information related to respective slope at both end sides of the signal waveform corresponding to each formed element contained in the urine specimen.

A second aspect of the present invention relates to a urine analyzer. The analyzer comprises: a flow cell through which a measurement sample containing a urine specimen flows; a light source arranged at a position for irradiating light on the measurement sample flowing through the flow cell; a light receiving part configured to generate a signal waveform indicating a temporal change of an intensity of light given off by the measurement sample; and a processing part configured to detect casts distinguishably from mucus threads contained in the urine specimen, based on information related to respective slope at both end sides of the signal waveform corresponding to each formed element contained in the urine specimen.

A third aspect of the present invention relates to a non-transitory computer-readable storage medium storing a program. The program causes a processor connected to an optical detector to execute operations comprising: instructing the optical detector to flow a measurement sample containing a urine specimen through a flow cell; instructing the optical detector to irradiate light on the measurement sample flowing through the flow cell; receiving, from the optical detector, a signal waveform indicating a temporal change of intensity of light given off by the measurement sample; and detecting casts distinguishably from mucus threads contained in the urine specimen, based on information related to respective slope at both end sides of the signal waveform corresponding to each formed element contained in the urine specimen.

DETAILED DESCRIPTION OF THE PREFERRED EMBODIMENTS

The preferred embodiments of the present invention are described hereinafter. Note that the following embodiments are merely illustrative. Note also that the present invention is not limited to the following embodiments.

First Embodiment (Urine Sample Analyzer 1)

Figure 1:
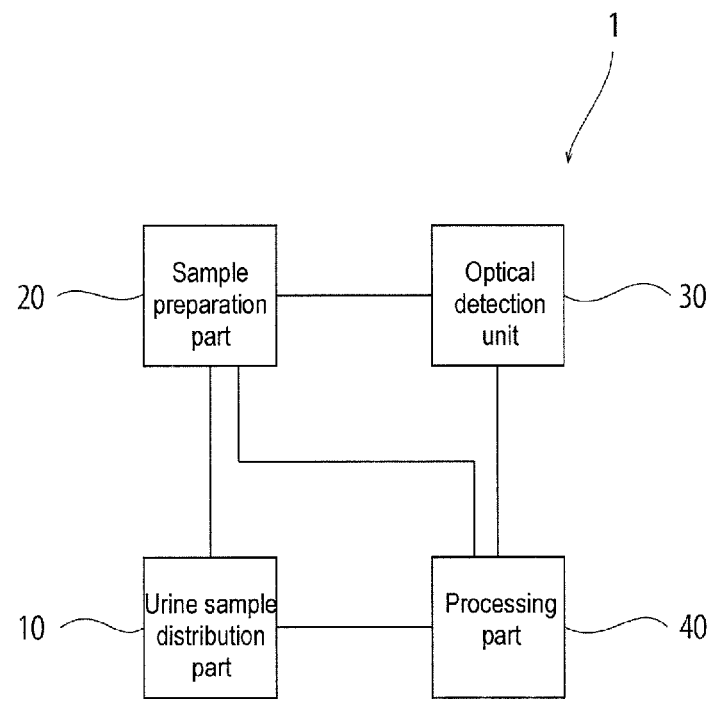
FIG. 1 is a brief block diagram of the urine sample analyzer of a first embodiment.

FIG. 1 is a brief block diagram of the urine sample analyzer 1 of a first embodiment. The urine sample analyzer 1 shown in FIG. 1 analyzes the formed elements in urine samples. Formed elements in urine samples include red blood cells, white blood cells, epithelial cells, bacteria, casts, and mucus threads. Casts are result of, for example, Tamm-Horsfall mucoprotein coagulating sedimentation in the renal tubular lumen. Blood cells and renal tubular epithelial cells are sometimes included in the substrate of the cast. Mucus threads include mucoprotein, and are long and thin formed elements.

The urine sample analyzer 1 has a urine sample distribution part 10, sample preparation part 20, optical detection unit 30, and processing part 40.

Figure 2:
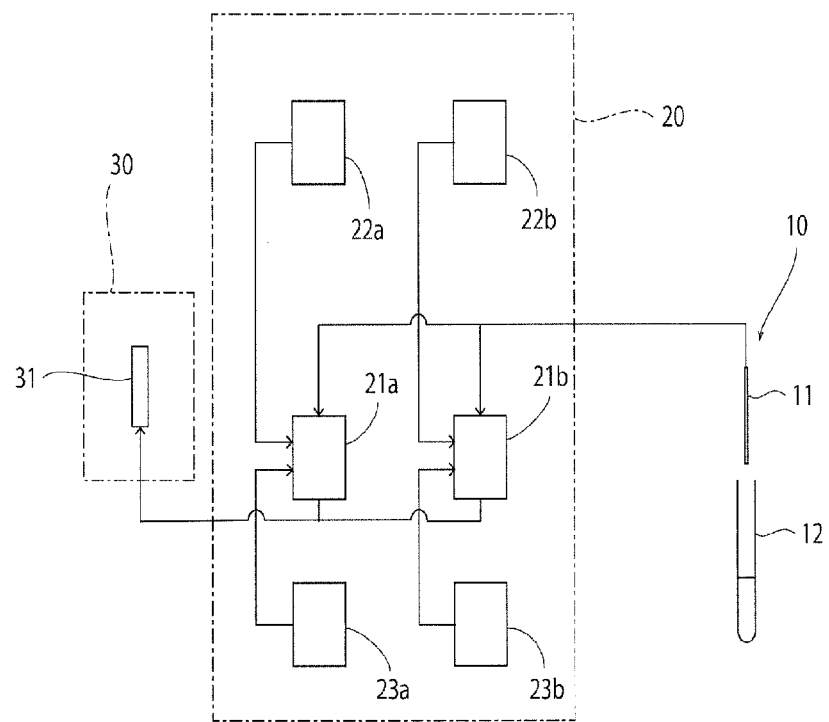
FIG. 2 is a schematic view of the urine sample distributing part and a measurement sample preparation part.

FIG. 2 is a schematic view of the urine sample distribution part 10 and the sample preparation part 20. As shown in FIG. 2, the urine sample distribution part 10 aspirates a predetermined amount of urine sample accommodated in a test tube 12 using an aspirating tube 11. The urine sample distribution part 10 dispenses the aspirated sample to the sample preparation part 20. Specifically, the urine sample distribution part 10 allocates urine sample aliquot to a first reaction tank 21a and a second reaction tank 21b of the sample preparation part 20.

In the first reaction tank 21a, the aliquot is mixed with a first diluting liquid 22a and a first staining liquid 23a. Hence, the formed elements in the measurement sample are stained by the colorant contained in the first staining liquid 23a. The first staining liquid 23a contains a staining dye which stains the cell membrane and proteins. A first measurement sample prepared in the first reaction tank 21a is supplied for analysis of particles that do not have nucleic acid, such as red blood cells, casts, mucus threads and the like, in urine.

In the second reaction tank 21b, the aliquot is mixed with a second diluting liquid 22b and a second staining liquid 23b. Hence, the formed elements in the measurement sample are stained by the colorant contained in the second staining liquid 23b. The second staining liquid 23b contains a staining dye which specifically stains nucleic acid. A second measurement sample prepared in the second reaction tank 21b is supplied for analysis of particles that have nucleic acid, such as white blood cells, epithelial cells, fungi, bacteria and the like, in urine.

The first and second reactor tanks 21a and 21b are respectively connected to the flow cell 31 of the optical detection unit 30. The first and second measurement samples are supplied from the first and second reaction tanks 21a and 21b to the flow cell 31. The measurement samples pass through the center of a pressurized sheath fluid flowing within the flow cell 31. A layered sheath flow is formed by the sheath fluid at this time. The formed elements contained in the measurement sample are drawn one by one into the layered sheath flow. The formed elements in the measurement sample pass through within the flow cell 31 one by one.

Figure 3:
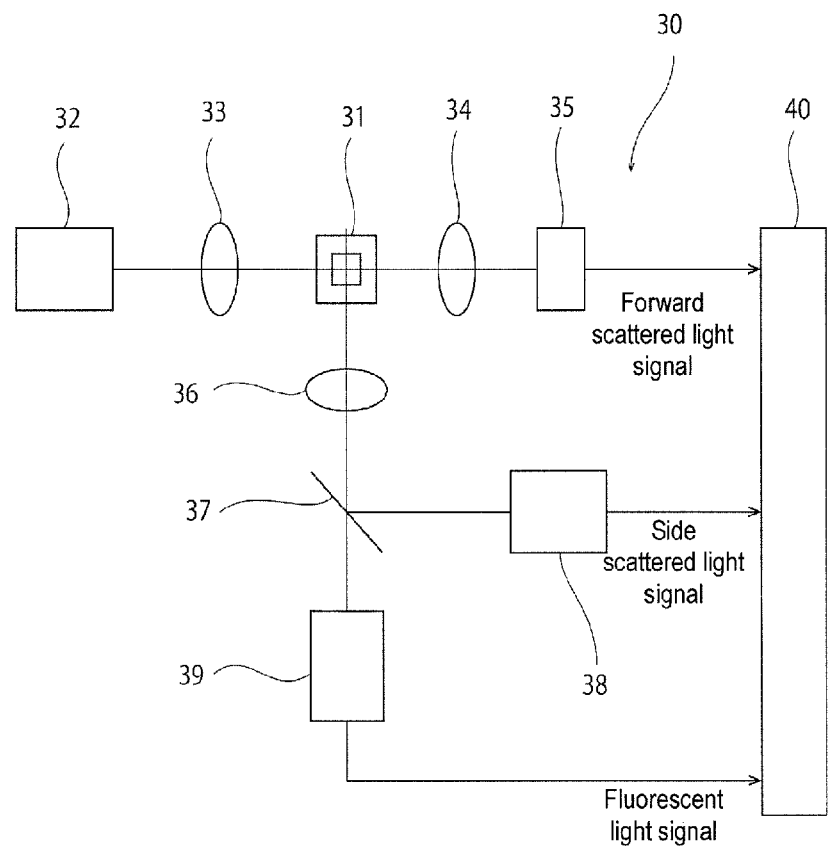
FIG. 3 is a schematic view of an optical detection part.

FIG. 3 is a schematic view of the optical detection part 30. As shown in FIG. 3, the optical detection part 30 has a light source 32. The light source 32 is configured by, for example, a semiconductor laser, gas laser or the like. The light from the light source 32 is condensed on the measurement sample flowing through the flow cell 31 via a condensing optical system 33. In this way the forward scattered light, side scattered light, and fluorescent light are given off from the formed elements contained in the measurement sample.

The forward scattered light is condensed on the light receiving part 35 of the optical system 34. The light receiving part 35 generates a forward scattered light signal (FSC) corresponding to the intensity of the received forward scattered light. The light receiving part 35 may be configured by, for example, a photodiode or the like.

The side scattered light is condensed on the light receiving part 38 by way of optical system 36 and dichroic mirror 37. The light receiving part 38 generates a side scattered light signal (SSC) corresponding to the intensity of the received side scattered light. The light receiving part 38 may be configured by, for example, a photomultiplier or the like.

The fluorescent light is condensed on the light receiving part 39 by way of optical system 36 and dichroic mirror 37. The light receiving part 39 generates a fluorescent light signal (FL) corresponding to the intensity of the received fluorescent light. The light receiving part 39 may be configured by, for example, a photomultiplier or the like.

The forward scattered light signal (FSC), side scattered light signal (SSC), and fluorescent light signal (FL) are respectively output to a processing part 40. The processing part 40 counts each of the formed elements using the forward scattered light signal (FSC), side scattered light signal (SSC), and fluorescent light signal (FL). The processing part 40 controls the urine sample distribution part 10, sample preparation part 20, and optical detection part 30. The processing part 40 includes a hard disc (memory) storing control programs for performing the control and analysis programs for identifying types of the formed elements, a CPU executing the programs read out from the hard disc, and so on.

(Urine Sample Analyzing Method Used in Urine Sample Analyzer 1)

Figure 4:
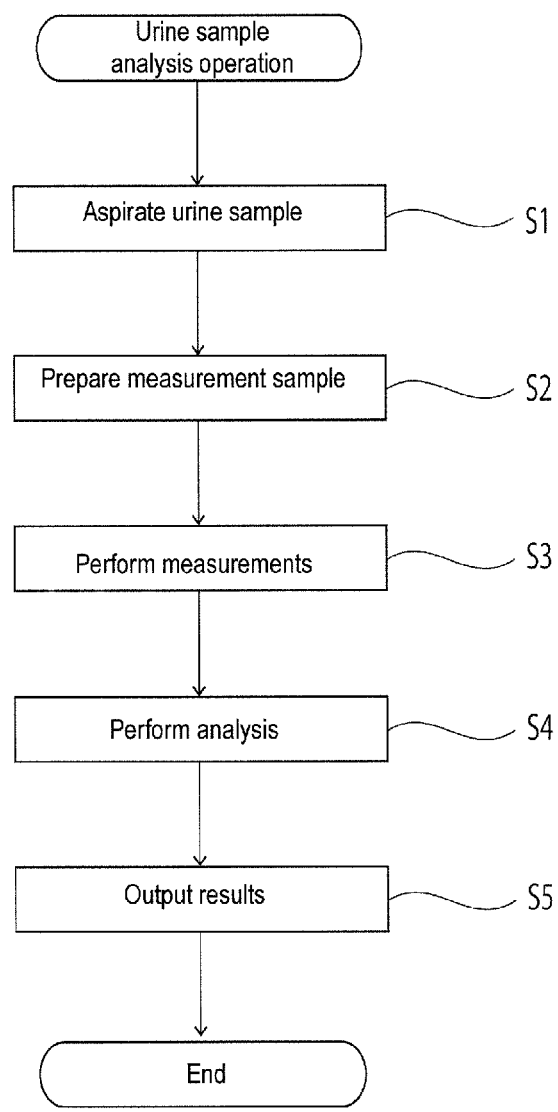
FIG. 4 is a flow chart of the urine sample analysis operation in the first embodiment.

In urine sample analyzer 1, the processing part 40 first controls the urine sample distribution part 10 and the sample preparation part 20 to prepare a measurement sample. Specifically, the processing part 40 controls the urine sample distribution part 10 to aspirate a sample (step S1), and controls the sample preparation part 20 to prepare a measurement samples from the aspirated sample, diluting liquids 22a and 22b, and staining liquids 23a and 23b (step S2), as shown in FIG. 4. As a result, a first measurement sample is prepared by mixing the first diluting liquid 22a and first staining liquid 23a with the urine sample, and a second measurement sample is prepared by mixing the second diluting liquid 22b and the second staining liquid 23b with the urine sample.

The processing part 40 then controls the optical detection part 30 to measure pursuant with the measurement items (step S3). The first measurement sample is supplied to the flow cell 31 while the sheath fluid is fed to the flow cell 31. The optical detection part 30 detects the forward scattered light, side scattered light, and fluorescent light, and generates forward scattered light signals (FSC), side scattered light signals (SSC), and fluorescent light signals (FL). The forward scattered light signal (FSC), side scattered light signal (SSC), and fluorescent light signal (FL) are respectively output to the processing part 40.

The second measurement sample is then supplied to the flow cell 31 while the sheath fluid is fed to the flow cell 31. The optical detection part 30 detects the forward scattered light, side scattered light, and fluorescent light, and generates forward scattered light signals (FSC), side scattered light signals (SSC), and fluorescent light signals (FL) according to the intensity of the light. The forward scattered light signal (FSC), side scattered light signal (SSC), and fluorescent light signal (FL) are respectively output to the processing part 40.

The processing part 40 analyzes the output signals (step S4). Specifically, the processing part 40 counts the formed elements such as red blood cells, white blood cells, epithelial cells, bacteria, casts, and mucus threads. The processing part 40 subsequently shows the analysis results on a display part which is not shown in the drawing (step S5).

The present embodiment is described in terms elan example in which the processing part 40 counts casts and mucus threads based on the fluorescent light signal (FL).

However, the present invention is not limited to this example. The processing part 40 also may be configured to specify formed elements using a signal other than the fluorescent light signal (FL). For example, the processing part 40 also may be configured to specify formed elements using signals related to the intensity of scattered light such as forward scattered light and side scattered light.

Figure 5:
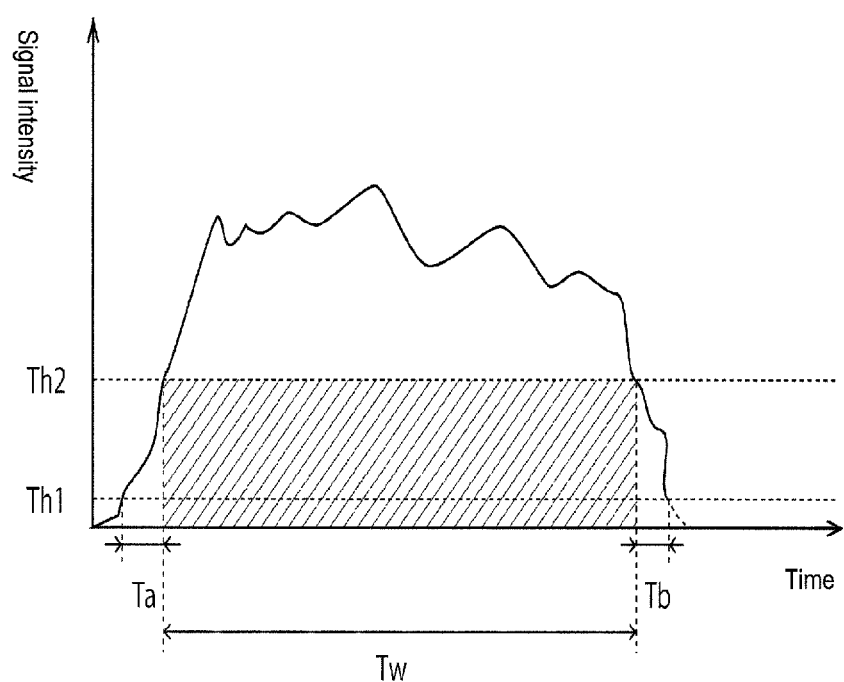
FIG. 5 is an example of a signal waveform on a time axis from a cast.

FIG. 5 is an example of a signal waveform on a time axis from a cast. The signal waveform indicates a temporal change of signal intensity obtained from the cast. Casts are generally thick, and have a uniform thickness. Therefore, casts have a large slope at both end s of the signal waveform on the time axis. That is, the bilateral ends are steep on the signal waveform on the time axis in the case of casts.

Figure 6:
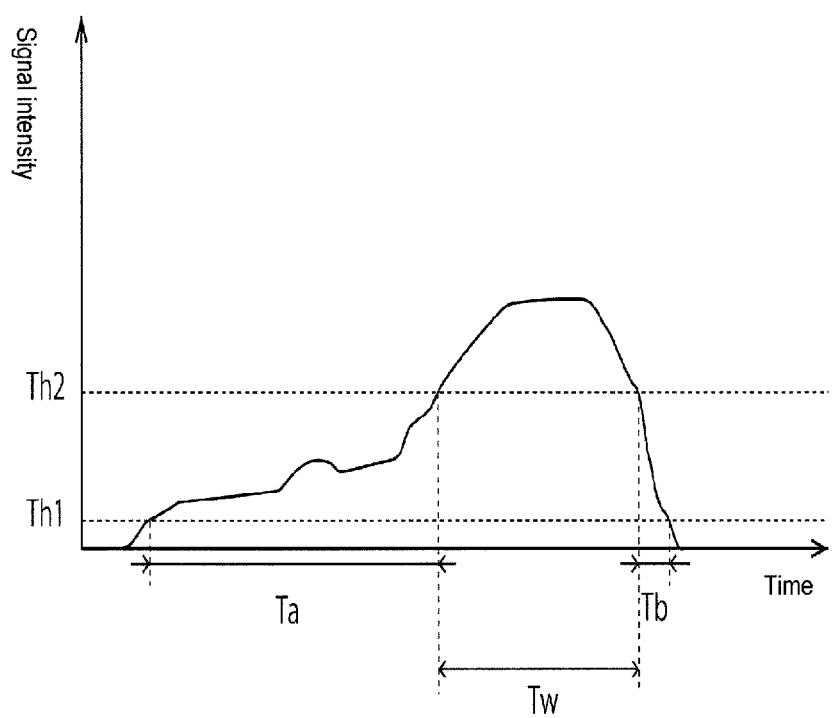
FIG. 6 is an example of a signal waveform on a time axis from a mucus thread.

FIG. 6 is an example of a signal waveform on a time axis from a mucus thread. The signal waveform indicates a temporal change of signal intensity obtained from the mucus thread. Mucus threads generally are thinner than casts, and have a narrow shape tapering from at least one end among a leading end and a trailing end. Therefore, mucus threads have a small slope at least at one end of the signal waveform on the time axis. Mucus threads also may have a steep slope at least at one end of the signal waveform on the time axis. FIG. 6 shows an example of the small slope at the leading end of the signal waveform of a mucus thread. The mucus thread signal waveform on a time axis includes signal waveforms which have a small slope at the trailing end, and signal waveforms which have a small slope at both the leading end and the trailing end.

Note that in the present specification the term "leading end" is defined as the downstream side of the flow cell 31 in the direction of the flow. Note also that in the present specification the term "trailing end" is defined as the upstream side of the flow cell 31 in the direction of flow.

In view of the characteristics of the signal waveform on the time axis corresponding to casts and mucus threads as described above, the processing part 40 of the urine analyzer 1 identifies the type of the formed element based on information related to the slope at least at one end of the signal waveform on the time axis corresponding to each formed element. Specifically, the processing part 40 determines that a formed element corresponding to a signal waveform having bilateral slopes that are smaller than a slope threshold value is a mucus thread based on information related to the slopes at bilateral ends of the signal waveform. The cast signal waveform does not satisfy the condition that at least the slope at one end is smaller than a slope threshold value. Therefore, the processing part 40 determines that a formed element corresponding to a signal waveform having bilateral slopes that are greater than a slope threshold value is a cast based on information related to the slopes at bilateral ends of the signal waveform. In this way casts and mucus threads contained in a urine sample can be discriminated with high degree of accuracy.

More specifically, the processing part 40 uses the time Ta from when the signal waveform initially attains the first signal level Th1 (refer to FIGS. 5 and 6) to the second signal level Th2 which is higher than the first signal level Th1, and the time Tb from when the signal waveform finally falls from the second signal level Th2 to the first signal level Th1 as information related to the slope of the ends of the signal waveform. The time Ta is a parameter representing the steepness of the slope at the leading end of the signal waveform. The time Tb is a parameter representing the steepness of the slope at the trailing end of the signal waveform.

Figure 7:
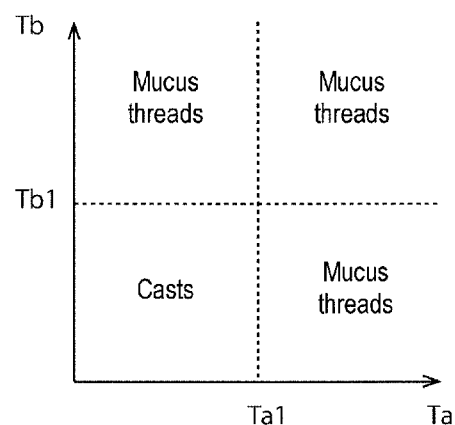
FIG. 7 is a graph representing the regions specifying the formed elements as cast or mucus thread in the first embodiment.

As shown in FIG. 7, the processing part 40 identifies a formed element as mucus thread when at least one of these conditions is satisfied: the time Ta is greater than a predetermined time Ta1, and a time Tb is greater than a predetermined time Tb1. That is, the processing part 40 identifies a formed element as a mucus thread when the condition Ta>Ta1 and Tb>Tb1 is satisfied, when Ta>Ta1 and Tb≤Tb1 is satisfied, and when Ta≤Ta1 and Tb>Tb1 is satisfied. The processing part 40 identifies a formed element as a cast when the condition Ta≤Ta1 and Tb≤Tb1 is satisfied.

Thus, the casts and mucus threads contained in the urine specimen are discriminated and detected based on information related to the respective slope at both ends of the waveform of the signal corresponding to each formed element contained in the urine specimen. Casts contained in a urine sample therefore are discriminated to a high degree.

Note that the first signal level Th1 may be, for example, approximately 3 to 10% of the maximum signal intensity. Further note that the second signal level Th2 may be, for example, approximately 50 to 80% of the maximum signal intensity.

Second Embodiment

Figure 8:
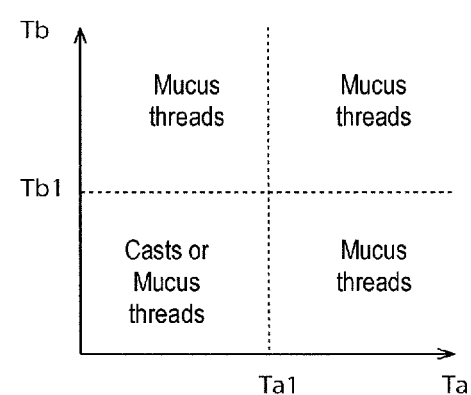
FIG. 8 is a graph representing the regions specifying the formed elements as cast or mucus thread in a second embodiment.

The first embodiment is described by way of example in which formed element is identified as a cast when the conditions Ta≤Ta1 and Tb≤Tb1 are satisfied. However, there may be times when all formed elements which have signal waveforms contained in this region cannot be identified as casts. For example, consider cases in which a plurality of mucus threads are entangled and form a single clot, and in which an impurity such as another cell is adhered to a mucus thread. In such cases there is a possibility that the conditions Ta≤Ta1 and Tb≤Tb1 may be satisfied even when the signal waveform is that of a mucus thread. In view of this possibility, the second embodiment also the possibility of a cast and the possibility of a mucus thread when the conditions Ta≤Ta1 and Tb≤Tb1 are satisfied, as shown in FIG. 8. Specifically, in this embodiment mucus threads contained in a urine sample are discriminated, and casts are detected based on information related to the respective slop at bilateral ends of the signal waveform, and information reflecting the shape of the part of the waveform which is not at either end of the signal waveform. In this way casts can be discriminated from mucus threads and detected with high identification accuracy. Note that the information reflecting the shape of the part of the waveform which is not at either end of the signal waveform also may be a parameter representing the correlation between the width of the signal waveform and the area of the signal waveform.

Figure 9:
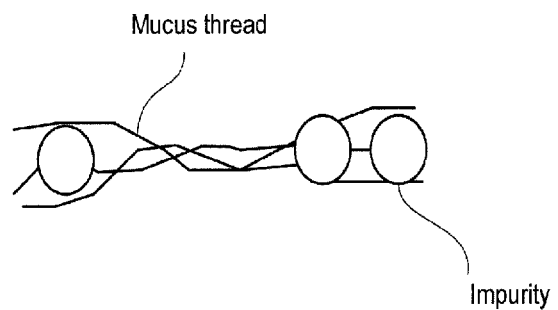
FIG. 9 is a schematic view showing an example a plurality of entangled mucus threads with other adhered impurities.

When, for example, impurities are adhered to both ends of a clot of a plurality of mutually entangled mucus threads as shown in FIG. 9, the signal waveform is steep at the bilateral ends of the waveform and the conditions Ta≤Ta1 and Tb≤Tb1 are satisfied. However, it is difficult to hypothesize that impurities are adhered to the entire mucus thread even in such cases. Therefore, clots that have a plurality of mucus threads generally have a part which is narrower than another part. In view of this possibility, a formed element is identified as a mucus thread when there is no predetermined correlation between the width Tw of the signal waveform and the area S of the signal waveform even when the respective slopes at the bilateral ends of the signal waveform are smaller than the slope threshold value. Hence, the processing part 40 identifies a formed element as a cast when the slopes at the respective bilateral ends of the signal waveform are less than the slope threshold value and there is a predetermined correlation between the width Tw of the signal waveform and the area S of the signal waveform.

That is, the processing part 40 identifies a formed element as a mucus thread when the condition Ta>Ta1 and Tb>Tb1 is satisfied, when the condition Ta>Ta1 and Tb≤Tb1 is satisfied, when the condition Ta≤Ta1 and Tb>Tb1 is satisfied, and when the condition Ta≤Ta1 and Tb≤Tb1 and there is no predetermined correlation between width Tw and area S is satisfied. The processing part 40 identifies a formed element as a cast when the condition Ta≤Ta1 and Tb≤Tb1 and there is a predetermined correlation between the width Tw and the area S is satisfied. Accordingly, the urine sample analyzer 1 identifies mucus threads and casts with higher accuracy.

Figure 10:
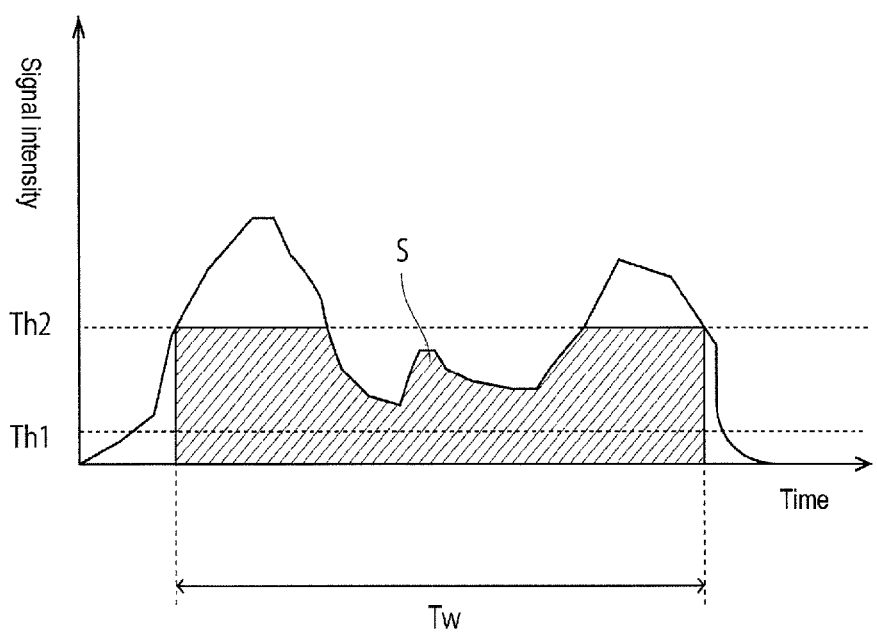
FIG. 10 shows an example of a signal waveform of a clot of plurality of entangled mucus threads with other adhered impurities.

Note that "width of the signal waveform" is the period from when the signal waveform initially attains the second signal level Th2 to when the signal waveform finally falls from the second signal level Th2, as shown in FIG. 10.

The area S is the area of the region (the hatch-marked region in FIG. 10) circumscribed by signal waveform and the straight line representing the signal intensity=0 in the period between when the signal waveform initially attains second signal level Th2 to when the signal waveform finally falls from the second signal level Th2.

The value R representing the correlation between the signal waveform width Tw and the signal waveform area S can be expressed as, for example, R=S/(Tw×h). Where h is a constant. The constant h is preferably the height of the second signal level Th2. The denominator (Tw×h) is equal to the area of the rectangle having the width Tw of the period from when the signal level initially exceeds the second signal level Th2 to when the signal level finally falls below the second signal level Th2, and a height Th2. That is, the denominator (Tw×h) is equal to the area S2 represented by the hatch marks of FIG. 5. Therefore, the equation can be expressed as R=S/S2.

In a clot formed by a plurality of mutually entangled mucus threads, a thin part readily occurs in the middle part in the length direction, as described above. In the case of casts, however, a thin part is unlikely to occur in the middle part in the length direction. Therefore, the area S will be small in the case of a mucus thread, and large in the case of a cast. The value R obtained by dividing the area S by the area S2 is a value approaching 1 in the case of casts, and a value less than 1 in the case of mucus threads.

Therefore, mucus threads and casts can be identified with high accuracy by comparing the threshold value R1 with the value R, which represents the correlation between the width Tw and the area S.

The threshold value R1 is preferably set, for example, at approximately 0.7. That is, when the area S1 is less than 70% of area S2, the formed element is preferably identified as mucus thread.

Other Embodiment

The value R which represents the correlation between the signal waveform width Tw and the signal waveform area S in the second embodiment also may be the ratio R2 of the signal waveform Tw and the signal waveform area S. For example, the ratio R2 also may be expressed as S/Tw. In this case, the ratio R2 is the maximum value Rmax when the signal level does not once fall below Th2 in the part that is not at the bilateral ends of the signal waveform, as shown in FIG. 5. Mucus threads and casts can be identified with high accuracy by comparing the ratio R2 and a threshold value R1. The threshold value R3 may be approximately 70% of the maximum value Rmax.

Figure 12:
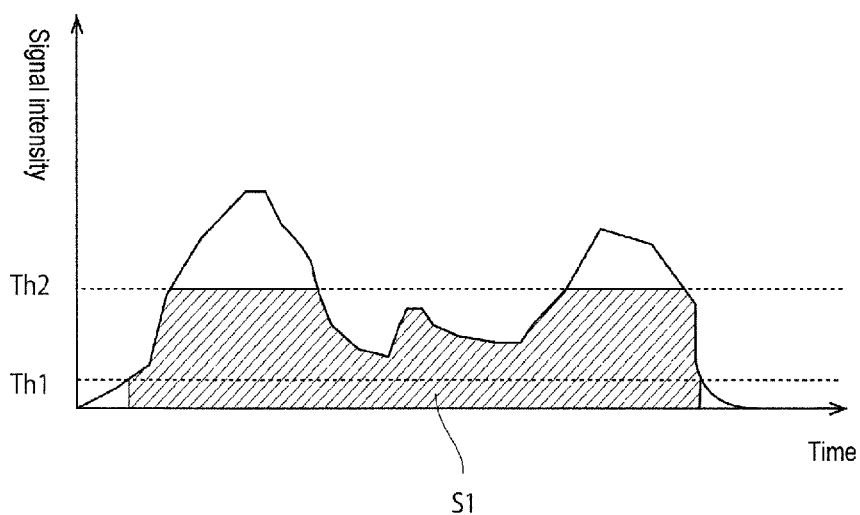
FIG. 12 shows an example of a signal waveform of a clot of a plurality of entangled mucus threads with other adhered impurities.

The signal waveform width Tw in the second embodiment, for example, also may be the period from when the signal waveform initially exceeds the signal level Th1 to when the signal waveform finally falls below the first signal level Th1. In this case, the area S of the signal waveform may be the area S1 of the region (the hatch-marked part in FIG. 12) in the period.

The second embodiment is described by way of example using a parameter representing the correlation between the signal waveform width Tw and the signal waveform area S to determine whether formed elements having a signal waveform which satisfies the condition Ta≤Ta1 and Tb≤Tb1 are casts or mucus threads. However, the present invention is not limited to this example. Other parameters also may be used as the information reflecting the shape of the part of the signal waveform which is not part of the bilateral ends of the signal waveform.

For example, information reflecting the thinness of the part which is thinner than the bilateral ends in the formed element may be used as another parameter.

The processing part 40 also may be configured to identify a formed element as a mucus thread when the slope at the bilateral ends of the signal waveform are respectively greater than a threshold value of the slope, and minimum value of the signal waveform is less than the threshold value of the signal waveform.

Figure 11:
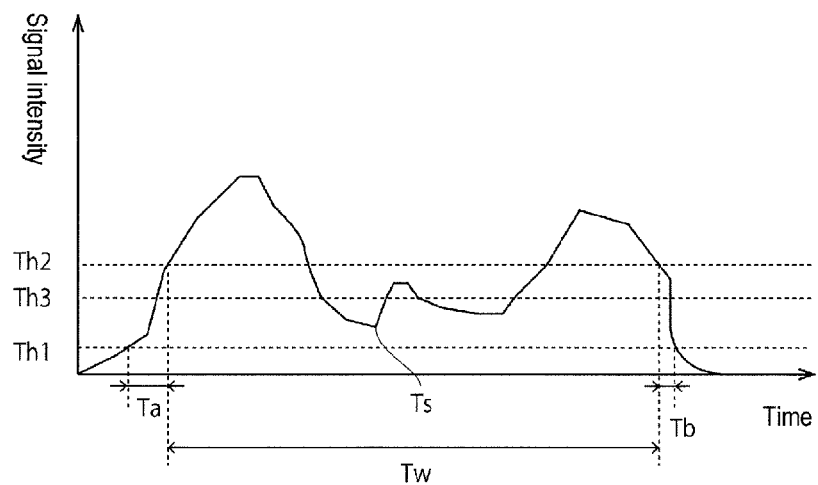
FIG. 11 shows an example of a signal waveform of a clot of a plurality of entangled mucus threads with other adhered impurities.

Referring to FIG. 11, for example, the processing part 40 also may be configured to identify a formed element as a mucus thread when the minimum value Ts of the signal waveform is less than a third signal level Th3. In this case the third signal level Th3 is preferably greater than the first signal level Th1, but less than the second signal level Th2. The third signal level Th3 is preferably, for example, approximately 20 to 30% of the maximum signal intensity.

For example, the minimum value may be the signal level when the signal level is lowest on the period from when the second signal level Th2 is initially exceeds to when the signal level finally falls below the second signal level Th2.

The processing part 40 also may be configured to identify a formed element as a cast when the slope at the bilateral ends of the signal waveform are respectively greater than a threshold value of the slope, and minimum value of the signal waveform is greater than the threshold value of the signal waveform.

For example, the processing part 40 also may be configured to identify a formed element as a casts when the condition Ta≤Ta1 and Tb≤Tb1 is satisfied and the minimum value Ts of the signal waveform is greater than the third signal level Th3.

In a clot formed by a plurality of mutually entangled mucus threads, a thin part readily occurs in the middle part in the length direction, as described above. The minimum value Ts reflects the thinness of the thin part in the middle part of the formed element. Accordingly, mucus threads and casts can be identified with high accuracy by determining the height of the minimum value Ts of the signal waveform relative to the third signal level Th3.

Note that the threshold value (Th3) relative to the minimum value Ts is not necessarily a fixed value. The threshold value (Th3) relative to the minimum value Ts also may be a variable value determined according to the signal waveform. For example, a specific value within a range of 10 to 20% of the maximum value of the waveform signal level may be used as the threshold value relative to the minimum value Ts.

The rate of reduction of the signal level in the part not at the bilateral ends also may be used instead of the minimum value as the information reflecting the thinness of the part which is thinner than the bilateral ends of the formed element. For example, the rate of reduction may represent the ratio of the minimum value Is determined as described above, and the maximum value of the signal level of the waveform.

The processing part 40 also may be configured to identify a formed element as a mucus thread when the slope of the respective bilateral ends of the signal waveform are greater than the slope threshold value, and the sum of the width of the part positioned in the period from when one signal level initially exceeds a threshold value to when one signal level finally falls, and the width of the part in which the signal level which has a signal level greater than one signal level is less than a threshold value, and this sum exceeds a threshold value.

Figure 13:
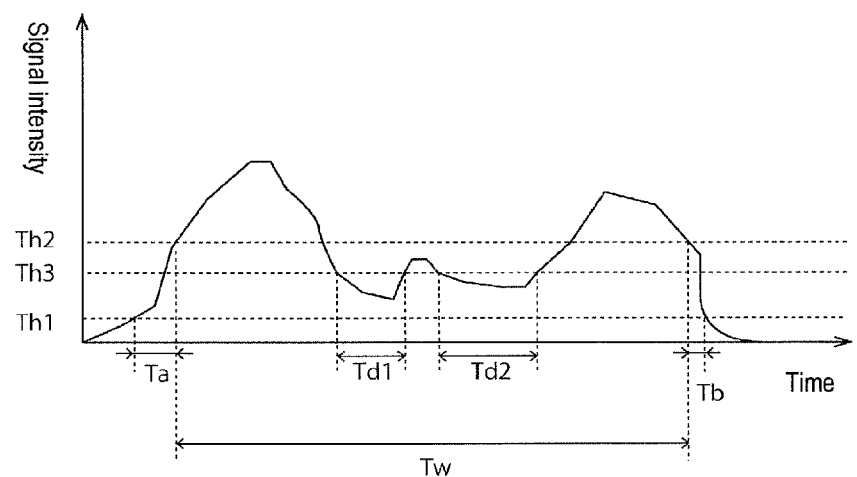
FIG. 13 shows an example of a signal waveform of a clot of a plurality of entangled mucus threads with other adhered impurities.

For example, referring to FIG. 13, the processing part 40 also may be configured to identify a formed element as a mucus thread when the sum Td, of the widths Td1 and Td2 of the parts positioned in the period from when the signal waveform initially exceeds the first signal level Th1 to when the signal waveform finally falls below the first signal level Th1 and is less than the third signal level Th3, is greater than the threshold value Tw1.

The processing part 40 also may be configured to identify a formed element as a cast when the slope of the respective bilateral ends of the signal waveform is greater than a slope threshold value, and the sum of the widths of the parts, positioned in the period among the waveforms from when the signal waveform initially exceeds one signal level to when the signal waveform finally falls below one signal level and the part is less than another signal level, is greater than a threshold value.

For example, the processing part 40 also may be configured to identify a formed element as a cast when the sum Td, of the widths Td1 and Td2 of the parts positioned in the period from when the signal waveform initially exceeds the first signal level Th1 to when the signal waveform finally falls below the first signal level Th1 and is less than the third signal level Th3, is less than the threshold value Tw1.

In a clot formed by a plurality of mutually entangled mucus threads, a thin part readily occurs in the middle part in the length direction, as described above. In the case of casts, however, a thin part is unlikely to occur in the middle part in the length direction. Therefore, the sum Td of the widths is larger in the case of mucus threads, and smaller in the case of casts. Therefore, mucus threads and casts can be identified with high accuracy by comparing the sum Td of the widths and the threshold value Tw1.

For example, the threshold value Tw1 preferably is approximately 30% of the width Tw (the period from when the waveform signal initially exceeds Th2 to when the signal finally falls below Th2) of the waveform signal.

The second embodiment is described by way of example using times Ta and Tb as the information related to the slope. In the present invention, other information also may be used as information related to slope.

Figure 14:
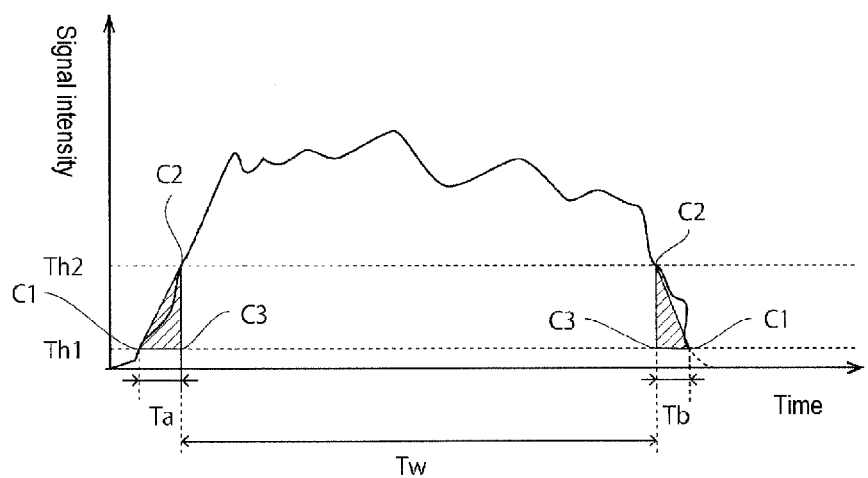
FIG. 14 is an example of a signal waveform on a time axis from a cast.

For example, referring to FIG. 14, the area of a triangle circumscribed by a first intersection point, a second intersection point, and a third intersection point also may be used as information related to slope when the intersection of the signal waveform and the first signal level Th1 is designated the first intersection point, the intersection of the signal waveform and the second signal level Th2 is designated the second intersection point, and the intersection of the first signal level Th1 and the time positioned at the second intersection point is designated the third intersection point.

Figure 15:
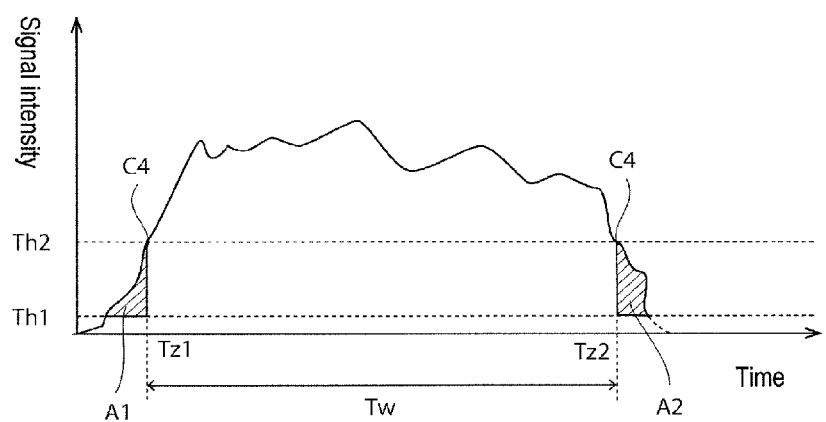
FIG. 15 is an example of a signal waveform on a time axis from a cast.

For example, referring to FIG. 15, the area of regions A1 and A2, which are circumscribed by time Tz1 and time Tz2 which are located at the intersection points C4 of the signal waveform and the first signal level Th1, and the signal waveform and the second signal Th2, also may be used as the information related to slope.

What is claimed is:
1. A urine specimen analyzing method comprising:
flowing a measurement sample containing a urine specimen through a flow cell;
irradiating light on the measurement sample flowing through the flow cell;
generating a signal waveform indicating a temporal change of intensity of light given off by the measurement sample; and
detecting casts distinguishably from mucus threads contained in the urine specimen, based on information related to respective slope at a leading end side and a trailing end side of the signal waveform corresponding to each formed element contained in the urine specimen, wherein the leading end side of the signal waveform represents a temporal change of signal intensity obtained from each formed element at a downstream side of the flow cell in the direction of flow and the trailing end side of the signal waveform represents a temporal change of signal intensity obtained from each formed element at an upstream side of the flow cell in the direction of flow;
wherein detecting the casts distinguishably from mucus threads comprises:
setting a first parameter representing the steepness of a first slope at the leading end side of the signal waveform;
setting a second parameter representing the steepness of a second slope at the trailing end side of the signal waveform;
wherein the first parameter corresponds to time from when the signal waveform rises from a first signal level to a second signal level higher than the first signal level, and
the second parameter corresponds to time from when the signal waveform finally falls from the second signal level to the first signal level; and
identifying the formed element as mucus threads upon determination that the first parameter is greater than a first threshold time, the second parameter is greater than a second threshold time, or both.

2. The urine specimen analyzing method of claim 1, wherein
the step of detecting the casts comprises identifying a formed element corresponding to a signal waveform as a mucus thread when at least one end side of the signal waveform has a slope less than a threshold value.

3. The urine specimen analyzing method of claim 1, wherein
the step of detecting the casts further comprises identifying a formed element as a cast upon determination that the first parameter is smaller than the first threshold time and the second parameter is smaller than the second threshold time.

4. The urine specimen analyzing method of claim 1, wherein
the step of detecting the casts is performed based on the information related to respective slope at the leading end side and the trailing end side of the signal waveform and information reflecting a shape of a part of the signal waveform which is different from either end side of the signal waveform.

5. The urine specimen analyzing method of claim 4, wherein
the information reflecting the shape of the part of the signal waveform is information representing a correlation between a width of the signal waveform and an area of the signal waveform.

6. The urine specimen analyzing method of claim 5, wherein
the information representing the correlation between the width of the signal waveform and the area of the signal waveform includes a value reflecting a ratio between the width of the signal waveform and the area of the signal waveform; and
the step of detecting the casts comprises identifying a formed element corresponding to a signal waveform as a cast when upon determination that the first parameter is smaller than the first threshold time and the second parameter is smaller than the second threshold time, and the value reflecting the ratio is greater than a threshold value.

7. The urine specimen analyzing method of claim 4, wherein
the information reflecting the shape of the part of the signal waveform is information reflecting a thinness of a part of the formed element which is thinner than both end sides of the formed element.

8. The urine specimen analyzing method of claim 7, wherein
the information reflecting the thinness includes a minimum value of a signal level of the signal waveform; and
the step of detecting the casts comprises identifying the formed element as a cast when each end side of the signal waveform has a slope greater than a threshold value, and the minimum value of the signal level of the signal waveform is greater than a threshold value.

9. The urine specimen analyzing method of claim 4, wherein
the information reflecting the shape of the part of the signal waveform includes a sum of widths of a part of the signal waveform where a signal level is less than a threshold value, excluding the both end sides of the signal waveform; and
the step of detecting the casts comprises identifying a formed element as a cast upon determination that the first parameter is smaller than the first threshold time and the second parameter is smaller than the second threshold time, and the sum of the widths of the part of the signal waveform is less than a threshold value.

10. The urine specimen analyzing method of claim 1, wherein
the information related to the slope includes a time from a first signal level until a second signal level is attained which is higher than the first signal level, or a time from the second signal level until the first signal level is attained.

11. The urine specimen analyzing method of claim 1, wherein
the information related to respective slope at the leading end side and the trailing end side of the signal waveform corresponding to each formed element contained in the urine specimen includes an area of a triangle circumscribed by a first intersection point, a second intersection point, and third intersection point,
wherein the first intersection point is an intersection point of the signal waveform and a first signal level;
the second intersection point is an intersection point of the signal waveform and a second signal level which is higher than the first signal level; and
the third intersection point is an intersection point of the first signal level and a time positioned at the second intersection point.

12. The urine specimen analyzing method of claim 1, wherein
the information related to respective slope at the leading end side and the trailing end side of the signal waveform corresponding to each formed element contained in the urine specimen includes an area of a region circumscribed by the signal waveform, a first signal level, and a time positioned at an intersection of the signal waveform and a second signal level which is higher than the first signal level.

13. The urine specimen analyzing method of claim 1, wherein
the step of generating the signal comprises generating the signal based on the intensity of a scattered light or fluorescent light from the measurement sample.

14. A urine analyzer comprising:
a flow cell through which a measurement sample containing a urine specimen flows;
a light source arranged at a position for irradiating light on the measurement sample flowing through the flow cell;
a light receiving part configured to generate a signal waveform indicating a temporal change of an intensity of light given off by the measurement sample; and
a processing part configured to detect casts distinguishably from mucus threads contained in the urine specimen, based on information related to respective slope at a leading end side and a trailing end side of the signal waveform corresponding to each formed element contained in the urine specimen, wherein the leading end side of the signal waveform represents a temporal change of signal intensity obtained from each formed element at a downstream side of the flow cell in the direction of flow and the trailing end side of the signal waveform represents a temporal change of signal intensity obtained from each formed element at an upstream side of the flow cell in the direction of flow;
wherein the processing part is further configured to detect casts distinguishably from mucus threads by:
setting a first parameter representing the steepness of a first slope at the leading end side of the signal waveform;
setting a second parameter representing the steepness of a second slope at the trailing end side of the signal waveform;
wherein the first parameter corresponds to time from when the signal waveform rises from a first signal level to a second signal level higher than the first signal level, and
the second parameter corresponds to time from when the signal waveform finally falls from the second signal level to the first signal level; and identifying the formed element as mucus threads upon determination that the first parameter is greater than a first threshold time, the second parameter is greater than a second threshold time, or both.

15. The urine analyzer of claim 14, wherein
the processing part identifies a formed element corresponding to a signal waveform as a mucus thread when at least one end side of the signal waveform has a slope less than a threshold value.

16. The urine analyzer of claim 14, wherein
the processing part identifies a formed element corresponding to a signal waveform as a cast upon determination that the first parameter is smaller than the first threshold time and the second parameter is smaller than the second threshold time.

17. The urine analyzer of claim 14, wherein
the processing part detects the casts distinguishably from the mucus threads, based on the information related to respective slope at the leading end side and the trailing end side of the signal waveform corresponding to each formed element contained in the urine specimen and information reflecting a shape of a part of the signal waveform which is different from either end side of the signal waveform.

18. The urine analyzer of claim 17, wherein
the information reflecting the shape of the part of the signal waveform is information representing a correlation between a width of the signal waveform and an area of the signal waveform.

19. The urine analyzer of claim 18, wherein
the information representing the correlation between the width of the signal waveform and the area of the signal waveform includes a value reflecting a ratio between the width of the signal waveform and the area of the signal waveform; and
the processing part identifies a formed element corresponding to a signal waveform as a cast upon determination that the first parameter is smaller than the first threshold time and the second parameter is smaller than the second threshold time and the value reflecting the ratio is greater than a predetermined threshold value.

20. A non-transitory computer-readable storage medium storing a program that, when executed by a processor, causes the processor connected to an optical detector to execute operations comprising:
instructing the optical detector to flow a measurement sample containing a urine specimen through a flow cell;
instructing the optical detector to irradiate light on the measurement sample flowing through the flow cell;
receiving, from the optical detector, a signal waveform indicating a temporal change of intensity of light given off by the measurement sample; and
detecting casts distinguishably from mucus threads contained in the urine specimen, based on information related to respective slope at a leading end side and a trailing end side of the signal waveform corresponding to each formed element contained in the urine specimen, wherein the leading end side of the signal waveform represents a temporal change of signal intensity obtained from each formed element at a downstream side of the flow cell in the direction of flow and the trailing end side of the signal waveform represents a temporal change of signal intensity obtained from each formed element at an upstream side of the flow cell in the direction of flow;
wherein detecting casts distinguishably from mucus threads further comprises:
setting a first parameter representing the steepness of a first slope at the leading end side of the signal waveform;
setting a second parameter representing the steepness of a second slope at the trailing end side of the signal waveform;
wherein the first parameter corresponds to time from when the signal waveform rises from a first signal level to a second signal level higher than the first signal level, and
the second parameter corresponds to time from when the signal waveform finally falls from the second signal level to the first signal level; and
identifying the formed element as mucus threads upon determination that the first parameter is greater than a first threshold time, the second parameter is greater than a second threshold time, or both.

* * * * *